United States Patent
Silva Ferreira et al.

(10) Patent No.: US 10,261,062 B2
(45) Date of Patent: Apr. 16, 2019

(54) METHOD FOR DETECTING A VOLATILE ANALYTE FOR CLASSING AND SORTING CORK STOPPERS DEPENDING ON THE CONCENTRATION OF THE ANALYTE

(71) Applicant: CORK SUPPLY PORTUGAL, SA, S. Paio de Oleiros (PT)

(72) Inventors: Antonio Cesar Silva Ferreira, S. Paio de Oleiro (PT); Ana Cristina De Avelar Lopes Cardoso, S. Paio de Oleiro (PT)

(73) Assignee: CORK SUPPLY PORTUGAL, SA, Paio de Oleiros (PT)

( * ) Notice: Subject to any disclaimer, the term of this patent is extended or adjusted under 35 U.S.C. 154(b) by 21 days.

(21) Appl. No.: 15/501,841

(22) PCT Filed: Dec. 17, 2015

(86) PCT No.: PCT/IB2015/059743
§ 371 (c)(1),
(2) Date: Feb. 5, 2017

(87) PCT Pub. No.: WO2016/098055
PCT Pub. Date: Jun. 23, 2016

(65) Prior Publication Data
US 2017/0241967 A1    Aug. 24, 2017

(30) Foreign Application Priority Data
Dec. 18, 2014 (PT) .......................................... 108104

(51) Int. Cl.
*G01N 33/00* (2006.01)
*G01N 1/22* (2006.01)
(Continued)

(52) U.S. Cl.
CPC ........ *G01N 33/0098* (2013.01); *G01N 1/2226* (2013.01); *G01N 15/0893* (2013.01);
(Continued)

(58) Field of Classification Search
CPC .... G01N 1/22; G01N 1/2226; G01N 33/0047; G01N 33/0052; G01N 33/0098;
(Continued)

(56) References Cited

U.S. PATENT DOCUMENTS 6,324,923 B1 * 12/2001 Dinsmore ............ G01N 1/2226
                                                                73/863.12
7,398,703 B2 * 7/2008 Nath ........................ G01N 1/40
                                                                73/23.35
(Continued)

FOREIGN PATENT DOCUMENTS

DE          3900799       *    6/1990

OTHER PUBLICATIONS

Boudaoud et al. Journal of Agricultural and Food Chemistry, vol. 51, 2003, pp. 1530-1533.*
(Continued)

*Primary Examiner* — Maureen Wallenhorst
(74) *Attorney, Agent, or Firm* — Mark M. Friedman

(57) ABSTRACT

A method for detecting a volatile analyte to class and sort cork stoppers depending on the concentration of the analyte, detection being preformed of concentrations in the order of ng/L (parts per trillion), in a concentrated gas applied to the cork stoppers in close containment. Cork stoppers are conveyed individually or groups to an incubation chamber; air/nitrogen is injected into the incubation chamber, the gas enriched with cork volatile compounds is entrained and carried to the concentration system containing a trap heated by desorption of entraining gas to a detection system recording a signal associated with presence of the analyte, the
(Continued)

signal being used for classing the stopper/groups of stoppers; a software receives and compares the signal with a minimum limit, deciding to approve or reject the stopper. A system for implementing this method is described.

8 Claims, 6 Drawing Sheets

(51) Int. Cl.
- *G01N 1/28* (2006.01)
- *G01N 1/40* (2006.01)
- *G01N 15/08* (2006.01)
- *B27K 7/00* (2006.01)
- *G01N 35/00* (2006.01)

(52) U.S. Cl.
CPC .......... *G01N 33/0047* (2013.01); *G01N 2035/00356* (2013.01)

(58) Field of Classification Search
CPC .......... G01N 15/0893; Y10T 436/19; Y10T 436/196666; Y10T 436/25; Y10T 436/25375; Y10T 436/255; Y10T 436/25875

USPC ....... 436/124, 126, 147, 174, 177, 178, 181; 422/83, 88

See application file for complete search history.

(56) References Cited

U.S. PATENT DOCUMENTS

| 2005/0092112 A1* | 5/2005 | Head | G01N 33/0034 |
| | | | 73/865.9 |
| 2015/0047414 A1* | 2/2015 | Riboulet | G01N 33/0011 |
| | | | 73/23.4 |

OTHER PUBLICATIONS

Mazzoleni et al. American Journal of Enology and Viticulture, vol. 45, No. 4, 1994, pp. 401-406.*

Lorenzo et al. Journal of Chromatography A, vol. 1114, 2006, pp. 250-254.*

Alvarez-Rodriguez et al. European Food Research Technology, vol. 230, 2009, pp. 135-143.*

* cited by examiner

METHOD FOR DETECTING A VOLATILE ANALYTE FOR CLASSING AND SORTING CORK STOPPERS DEPENDING ON THE CONCENTRATION OF THE ANALYTE

FIELD OF THE INVENTION

This invention falls within the scope of the methods for the analysis of volatile compounds, with the present case showing as an example of chemical species to be detected the 2,4,6-trichloroanisole (TCA). The method for detection disclosed in this invention uses a concentration system which allows concentration ranges of ng/L to be reached, with little or no use of other separation techniques such as chromatography. In the said example, TCA is detected in a closed conditioning system, with the aid of high-speed chromatography, with high output, and in the aforementioned concentrations of parts per trillion (ppt) equivalent to ng/L. Categorization and separation of the cork stoppers are also performed according to the parameters which were defined as levels of acceptance of the said analyte. The currently used method is compatible with the industry requirements, since it provides the analysis of 1000 to 10000 cork stoppers per hour.

BACKGROUND OF THE INVENTION

Portugal is the largest cork producer and processor worldwide. Today, cork stoppers account for the highest sales volume in the cork industry. The economic valorisation of cork stoppers will enable a sustainable maintenance and exploitation of the cork oak plantation, also contributing to biodiversity preservation, $CO_2$ fixation, and creation of local employment.

However, although cork stoppers contain unique properties, a percentage of them give the so-called "cork taste" to the wine, a very unpleasant (smell and taste) organoleptic defect, which reduces the wine quality and its acceptance by the consumers, thus causing serious losses to the relevant wine brand and, consequently, to the cork sector.

Several organohalogenated compounds, in particular 2,4,6-trichloroanisole (TCA), have been described as responsible for giving the wine some unpleasant organoleptic properties. Cork stoppers have been pointed out as being at the root of that contamination.

TCA has been identified as the main responsible for the problem of "cork taste" in the wine for the first time by Tanner et al. in 1982, and although a relation has also been established between other aromatic compounds and this defect (Simpson, 2004; Pena-Neira 2000; Chatonnet, 2004), TCA is generally considered as the best indicator of problems in the wine (Herv é, 2000). According to the European project Quercus, the presence of TCA was detected in at least 80% of the wines with "cork taste". In addition to this, TCA is a compound whose sensorial detection limit is set in very low concentrations, in the range of nanograms per liter of wine (Amon, 1989; Tanner, 1982).

Other organochlorine compounds are also highlighted, such as 2,4,6-trichloroanisole (2,4,6-TCA), 2,3,4,6-tetrachloroanisole (TeCA), pentachloroanisole (PCA), 2,4-dichloroanisole (2,4-DCA), 2,6-dichloroanisole (2,6-DCA), 2,4,6-trichlorophenol (2,4,6-TCP), 2,3,4,6-tetrachlorophenol (2,3,4,6-TCP), 2,4,6-tribromoanisole (2,4,6-TBA) and pentachlorophenol (PCP); from other chemical groups, there are compounds such as 2-methoxy-3,5-dimethylpyrazine (MDMP), guaiacole, geosmine, 2-methyl-isoborneol and 1-octen-3-ol. Significantly, 80 to 85% of the so-called "cork taste" is attributed to the presence of 2,4,6-trichloroanisole (2,4,6-TCA). In this context, eliminating those contaminants in general, and 2,4,6-TCA in particular, from the cork stoppers is extremely important for the cork industry.

The presence of TCA in the cork stopper has been the object of several studies (Silva Pereira, 2000), along with the development of processes intended for treating and mitigating the damage (Gil, 2006). The direct precursors of chloroanisoles are chlorophenols which are converted into chloroanisoles by means of a methylation reaction carried out by some microorganisms, especially fungi under specific conditions of temperature and pressure (Insa, 2006). Therefore, chlorophenols are a potential source of TCA.

The true origin of the organochloride compounds—TCA precursors—found in the cork not being clarified yet, efforts have been focused in the development of methods aimed at removing the said compounds from cork stoppers.

The use of extraction processes is herein highlighted, which are basically focused in procedures intended for the removal of chlorinated compounds from cork by means of extraction/washing with solvents, evaporation or degradation, upon the manufacturing.

The patent WO 2004014436 relates to the extraction of compounds dragged in water vapour from cork granulates, with extraction efficiencies of up to 90% or, as mentioned in the patent WO 03041927, the extraction by ethanol/water in the vapour phase, in natural cork stoppers requiring special care in order to preserve its mechanical, physical and functional properties, with an extraction efficiency of up to 80%.

The patent FR19990012003 discloses an invention in which is perfectly clear that the cork is subject to supercritical extraction, always in the form of board or granulate and not in the form of cork stopper. Actually, in the whole document there is no reference made to the process being directly applied to the natural cork stopper; a publication by Eduard Lack, in 2006, at the $3^{rd}$ International Meeting of Chemical Engineering and High Pressure, on behalf of NATEX, the Austrian company which leads the project and the construction of the industrial facilities where the patented supercritical extraction process is carried out, states that during the depressurization step the cork stoppers do not return to their original shape. So, the author concludes that it is impossible to apply this kind of treatment to the natural cork stopper. Furthermore, the author specifies that the treatment with supercritical fluids shall be directly applied to the cork granulate and that cork stoppers must be produced a posteriori.

The extraction with n-pentane in soxhlet is also known, which although effective (being used in laboratory for the analysis of 2,4,6-TCA by GC) involves a very expensive industrial technology (implementation and maintenance), also implying risks related to the solvent's handling and to a possible contamination of the cork.

Microwaves are also used, so that the temperature is increased and the evaporation of the contaminants is made easier. However, 2,4,6-TCA, just like most of trichloroanisoles, has a low volatility (boiling point=240° C.) and is strongly adsorbed to the cork's cellulose, lignin and suberin macromolecules, which makes it hardly dry-desorbed by evaporation. On the other hand, as cork is an excellent thermal insulator, high external temperatures must be used in order to attain the desired internal temperature (which is lower), except in the case where microwaves are used, which can cause an outer deterioration and refraction, with the release of inner compounds becoming more difficult.

In a distinct approach, the irradiation of the cork, namely with gamma radiation (Co60, 15 KGy) (PT103006), ionizing radiation or electron beam, is used for reducing the microbiological contamination (sterilization). These techniques also cause (depending on the dose) the contaminants to degrade, generally transforming them in molecular waste with no smell. However, although the sterilization leads to a decrease in the formation of 2,4,6-TCA and the technique is also susceptible of providing degradation of contaminants, the latter is only partial and the toxicity of the degradation products is unknown. But, above all, those techniques are expensive and, in practical terms, they are impossible to implement in the industry, either due to imposed costs and technical complexity, or to the costs associated to an eventual service being provided.

The use of ozone (Vlachos, 2007), ultrasounds (Penn, C, 2004) and photodegradation (Vlachos, 2008) have been also described.

The use of enzymes for the phenol inactivation has also been tested, namely phenol-oxidase, such as suberaseT (Novozyme). This enzyme promotes the phenol polymerisation, but the strategy has shown to be of very low efficiency as regards the elimination of the "cork taste".

Another proposed strategy is based on the use of fungi which can inhibit the development of other populations that have been mentioned as being susceptible of conferring unpleasant properties to the cork or whose metabolism can degrade the compounds involved in this contamination process.

In the patent WO2008042181 another technique is mentioned in which the coating of the cork stoppers has a thin film of silicone aimed at 'encapsulating' the contaminants thus avoiding their migration. Although simple and not much expensive, the technique proved to be ineffective since most of the cork stoppers undergo a final treatment with paraffins and silicones for purposes of adorning, as well as easing the operation of the cork machine. On the other hand, there is a risk of the contaminants passing from the polymer to the liquid medium when in contact, or even a problem of durability of the coating layer, the treatment of the surface with silicone.

In contrast, over the last 20 years, scientific evidence has been gathered which suggests that the organohalogenated compounds found in nature are extensively produced by microorganisms, namely soil bacteria, yeasts, moulds and filamentous fungi. Most of the organohalogenated compounds produced are environmentally harmless, due to their slow degradation, but some of them have biological activity, thus inhibiting for example the growth of competitive microorganisms. And this is the reason why, in another approach, the development of formulations was sought in such a way as to include the inhibitor(s) of the enzymes that are directly or indirectly involved in the formation of the precursor 2,4,6-TCP.

Furthermore, although some of the aforementioned inventions do contribute to reduce the content of contaminants in the cork stopper, none of the disclosed methods shows to fully prevent their transmission to the wine.

A different perspective is based upon non-invasive and non-destructive control methods, an example of which is the patent WO2011078714. In effect, the heterogeneous character of cork, characteristic of natural products in whose complexity participate inter alia physiological, biological and climatic factors, causes the statistical control, although being relevant to the development and support of a controlled process, to always make available limited information in what concerns the quality of the product. The market requirements as regards the bottle to bottle—stopper to stopper—warranty cannot be attained by the statistical control.

However, this kind of approach is not duly explored in what concerns sensorial deviations in cork stoppers. The patent application WO2005047853 was identified, which relates to the same issue but proposes a different solution from the one disclosed in this invention, mentioning the use of 'nose chips' for detection of an analyte in cork stoppers, the said patent not having as object the rhythm of the performed analysis, which is crucial in order to attain the industrial objectives.

The inspection of cork stoppers according to their sensorial quality—the presence of sensorially offensive compounds—is also described in the patent US2008245132. However, this patent only describes a possible classification process, without any specific description of an analytic solution and synchronization of the required events in that scope. Therefore, this patent contains elements which are much more evolved as regards the operation of a 100% and non-destructive inspection in batches of cork stoppers.

The patent WO2004004995 was also identified, in which a decontamination process of the cork is mentioned (TCA and chlorophenols), however not having as its object the inspection, categorization and separation of the unaccepted cork stoppers.

In the patent US2009180122, a method is used for the analysis of a sample by means of fast-scan continuous wave terahertz spectroscopy which is intended for the non-destructive assessment of materials, such as animal skin and natural cork, as well as for the detection of explosives, concealed weapons and narcotic drugs.

Finally, the patent WO2004076607 was also identified, which relates to a process for preventing the cork stoppers' flavours from being transferred to the wine, by the use of a membrane.

BRIEF DESCRIPTION OF THE FIGURES

The FIGS. 1a, 1b, 1c and 1d represent the operation of the method for detection of the volatile analyte.
(1)—incubation chamber—each circle in FIG. 1b represents one incubation unit, in different steps of the analytical cycle, being synchronized as described in FIG. 4
(2)—selector valve of the gas flow from the incubation chamber (1) to the trap (4)
(3)—selector valve (3) for sending gas stream to the detector line or for cleaning the circuit
(4)—trap
(5)—selector valve (5) of the gas flow from the trap (4), of multiple units, to the detection system (6)
(6)—detector
(7)—selector valve of the circuit to be used to send the volatile compounds for analysis
(8)—vacuum pump
(9)—controller;
(A)—supply of cork stoppers
(G)—assembly containing N incubation chambers More specifically, FIG. 1a relates to the first step of the detection method, namely ventilation.

SUMMARY OF THE INVENTION

Figure 1A:
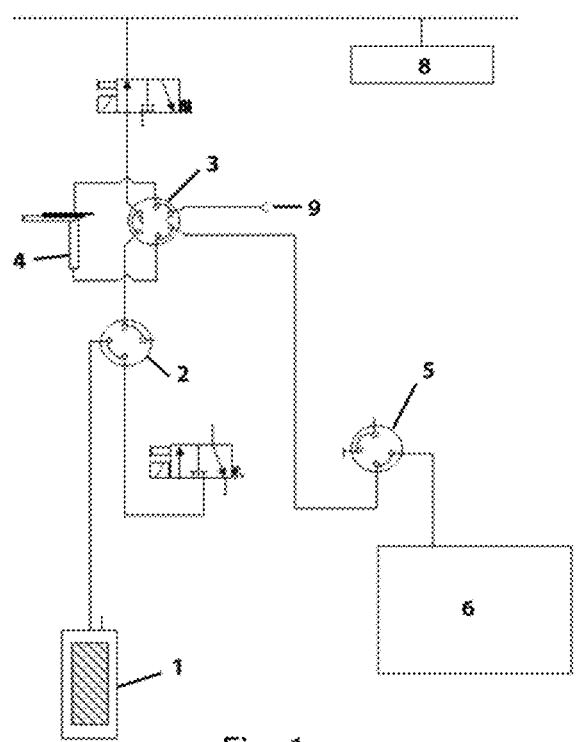
FIG. 1b represents the second step and relates to the connection between the trap and the compartment with the stoppers, wherein the vacuum is previously established for a pre-determined period of time.
FIG. 1c represents the third step of the method and relates to the heating of the trap at pre-established conditions of temperature and time; at last.
FIG. 1d represents the fourth step and relates to the valve (3) (six-part valve) which connects the trap to the controller (9) and to the detector, with heating of the trap.
Figure 1B:
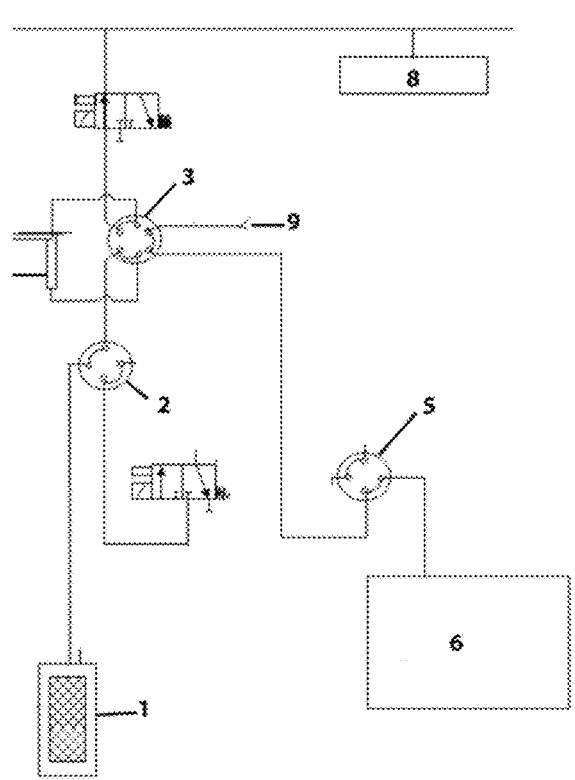
Figure 1C:
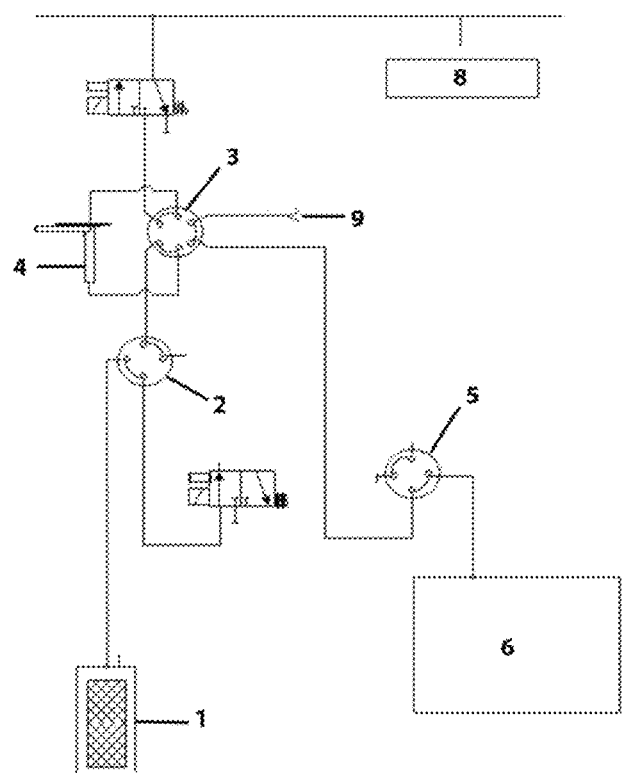
Figure 1D:
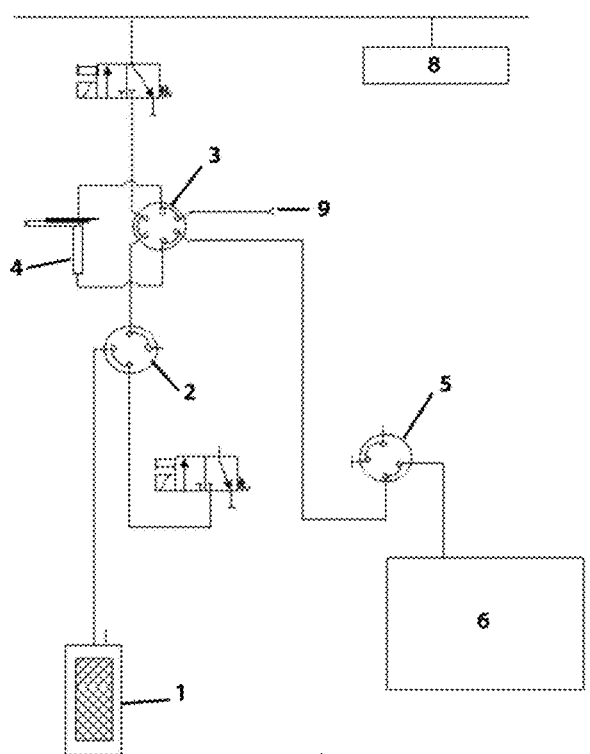
Figure 2A:
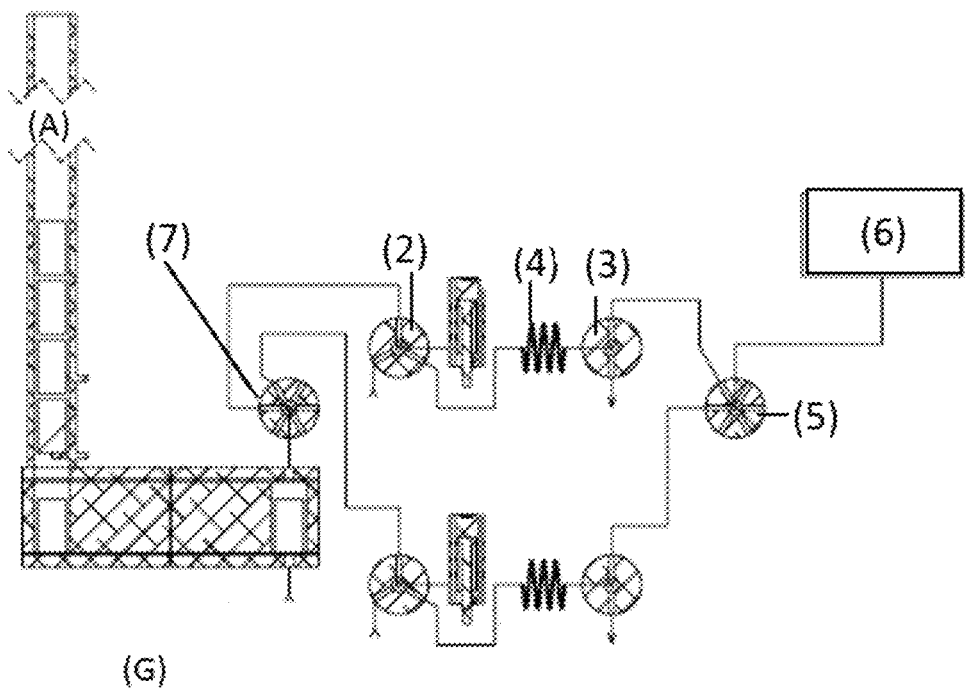
FIG. 2a: Operation of the method for detection of the volatile analyte using a conception illustrated in FIG. 3, with the following references:
(1)—incubation chamber—each circle in the figure on the right represents one incubation unit, in different steps of the analytical cycle, being synchronized as described in FIG. 4;
(2)—selector valve of the gas flow from the incubation chamber (1) to the trap (4);
(3)—selector valve for sending gas stream to the detector line or for cleaning the circuit;
(4)—trap;
(5)—selector valve of the gas flow from the trap (4), of multiple units, to the detection system (6);
(6)—detection system;
(7)—selector valve of the circuit to be used to send the volatile compounds for analysis;
(A)—supply of cork stoppers
(G)—assembly containing N incubation chambers
Figure 2B:
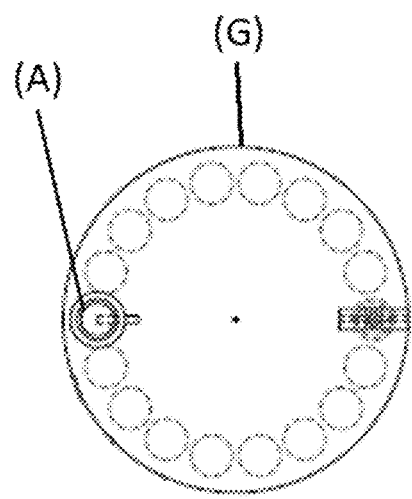
FIG. 2b: Detailed view of the incubation set and wherein each circle of the figure on the right represents one incubation unit, in different steps of the analytical cycle, being synchronized as described in FIG. 4, with the following references:
(A)—supply of cork stoppers
(G)—assembly containing N incubation chambers
Figure 3:
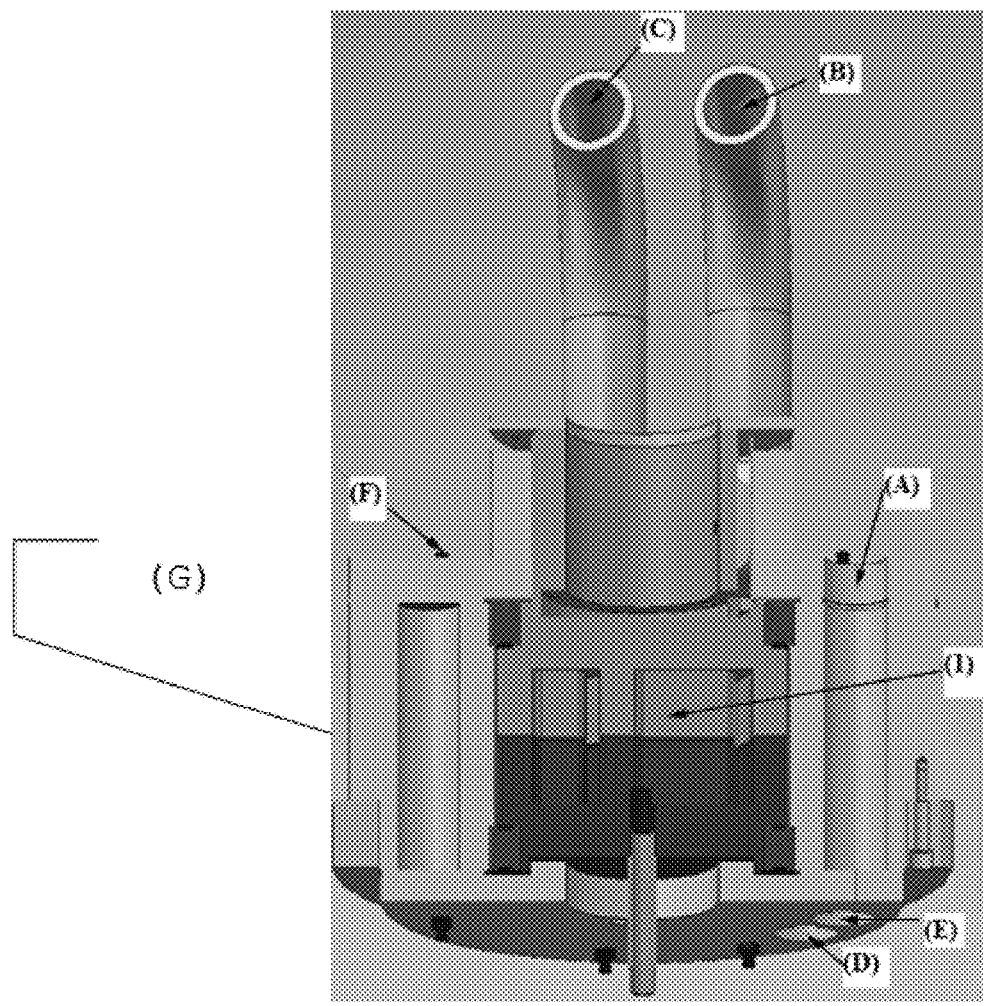
FIG. 3: Example of the conception of a system for the analysis of volatile compounds in cork stoppers to the pilot-scale, with the following references:
(1)—incubation chamber
(A)—supply of cork stoppers
(B)—exit for cork stopper or group of cork stoppers with a positive result in the presence of the analyte
(C)—exit for cork stopper or group of cork stoppers with a negative result in the presence of the analyte
(D)—exit of cork stopper or group of cork stoppers for which the analysis has generated any kind of error
(E)—position in the proposed configuration wherein the incubation chamber is cleaned before entering new cork stoppers
(F)—suction point from the sample (gas containing the analyte) to the trap
(G)—assembly containing N incubation chambers
Figure 4:
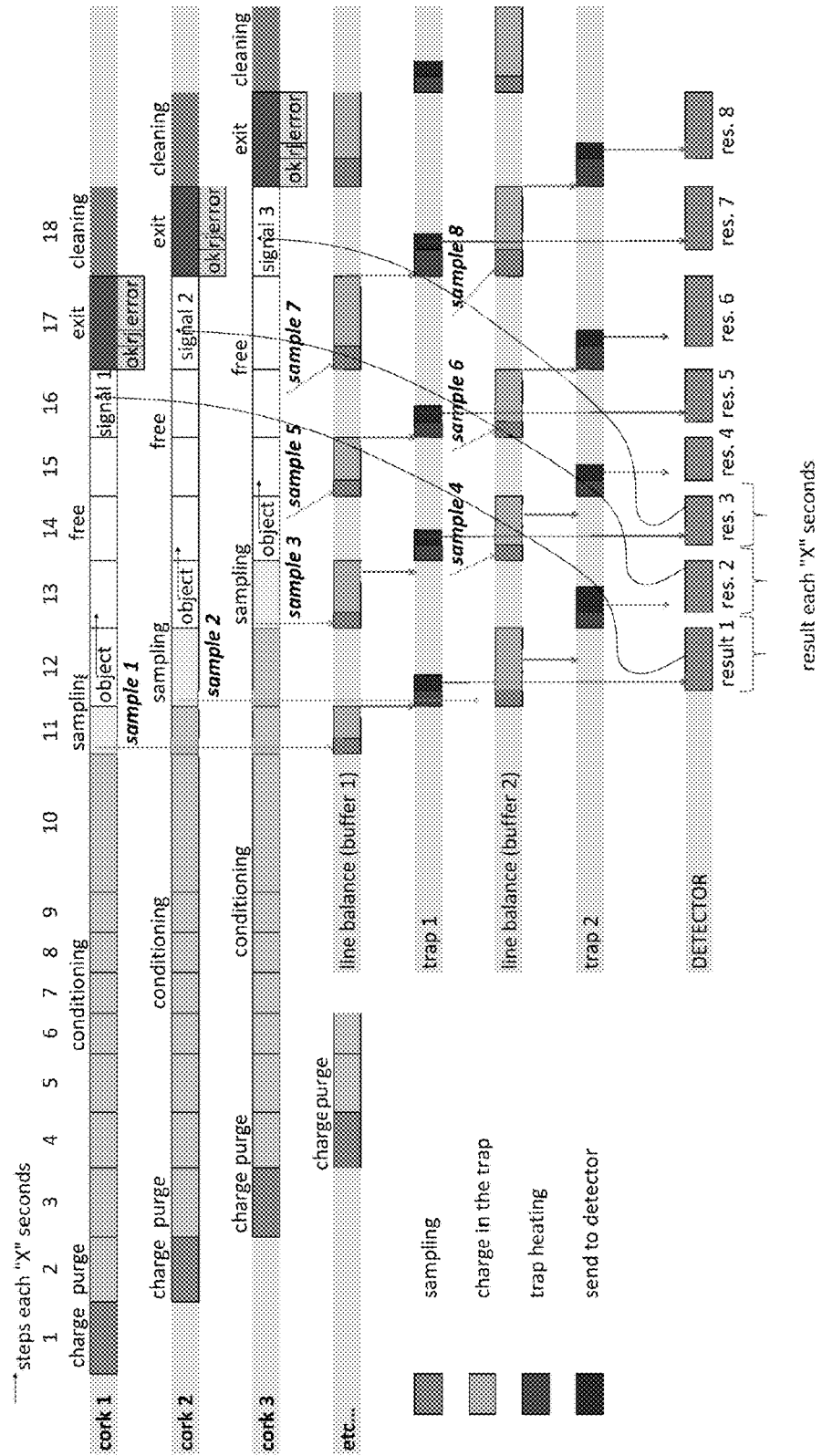
FIG. 4: Synchronization of events using a proposed configuration
Figure 5:
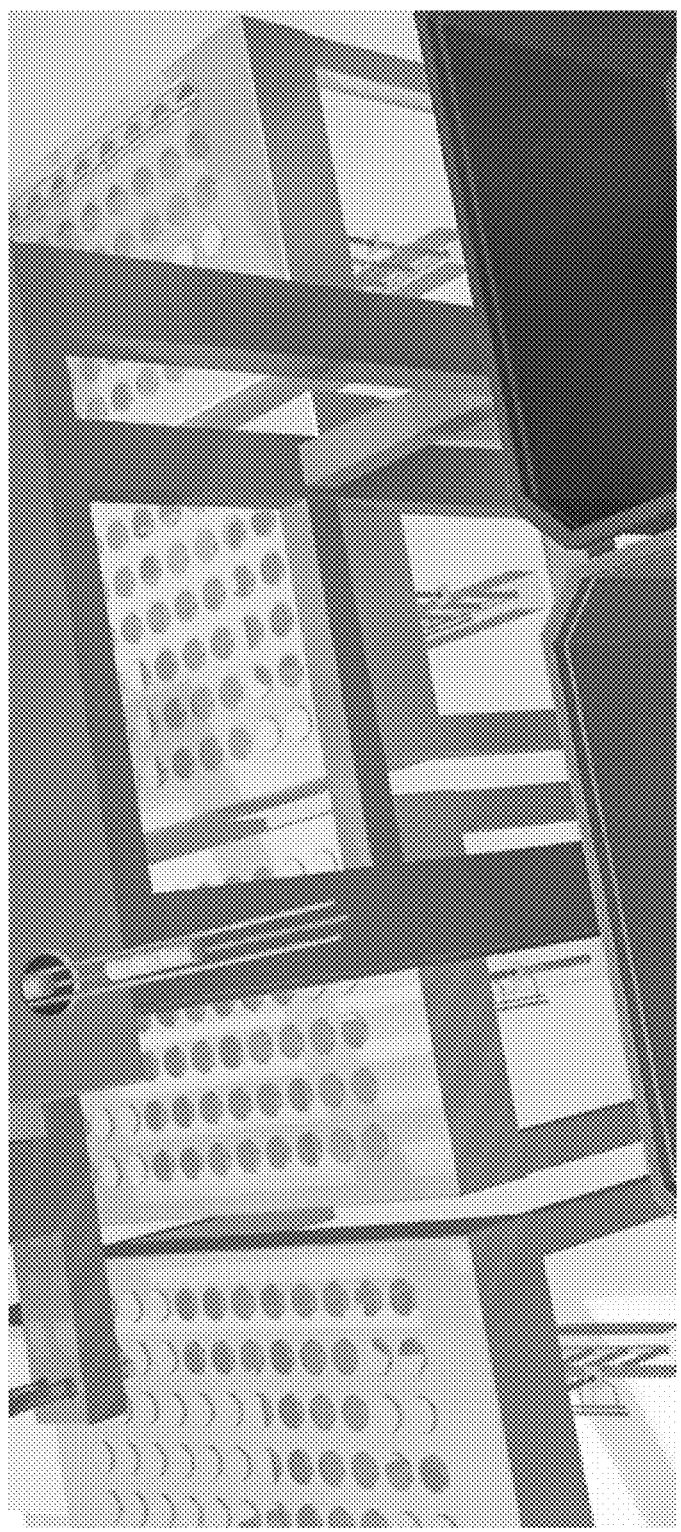
FIG. 5: Representation of an installation for industrial processing

This invention relates to a method which allows the volatile analyte to be detected, in this particular case the 2,4,6-trichloroanisole (TCA), by means of a non-invasive and non-destructive proceeding, the said analyte being possibly found in very low concentrations (ppt) and accumulating in the gaseous phase over cork stoppers and confined to a closed conditioning system. This invention provides categorization and separation of the cork stoppers according to parameters established as the levels of acceptance of the said analyte.

The technical solution presented also offers a rhythm which is compatible with the industrial needs, since it allows 1,000 to 10,000 cork stoppers to be analysed on an hourly basis.

The perspective disclosed by this invention is based upon non-invasive and non-destructive controlling methods, an approach that is essential considering the heterogeneous character of the cork as well as the market requirements concerning the bottle-to-bottle—i.e., stopper-to-stopper—warranty, which are not compatible with the statistical control.

Although the cork industry has developed preventive and curative procedures aimed at avoiding the presence of compounds with organoleptic impact, traces of those compounds still continue to be detected in cork stoppers.

In particular, the presence of TCA is hardly avoided due to the combination of factors such as:
1. the waterproofing properties of cork;
2. the need to reach concentration values within the range of ppt, an extraordinarily low value, due to the compound's low sensorial perception threshold;
3. the compound's high chemical stability.

In the industrial scope, cork stoppers are subject to washing which can be made by using oxygenated water or peracetic acid, for cleaning and disinfecting purposes. After washing/disinfection, the humidity content is stabilized, thus providing an optimal performance of the stopper as sealant and simultaneously reducing the microbiological contamination. However, as regards the issue of volatile compounds, namely TCA, these methods are not enough (Gil, 2006).

This invention also allows to:
Reduce the energy consumption associated to techniques intended for extracting 2,4,6-TCA from the cork;
Carry out a 100% control in the batches of cork stoppers, in a rhythm which is compatible with the industrial activity;
Ensure levels of contamination which are under the sensorial detection limit.

DETAILED DESCRIPTION OF THE INVENTION

This invention relates to the detection of a volatile analyte in cork stoppers by means of a non-destructive and non-invasive methodology in which the said analyte is detected in concentrations within the range of ng/l (parts per trillion—ppt), as well as to the inspection and categorization of the cork stoppers according to the parameters defined as the acceptance levels of the said analyte, offering the possibility of analysing 1,000 to 10,000 cork stoppers on an hourly basis. In this particular case, the analyte to be detected is 2,4,6-trichloro-anisole (TCA).

Comparatively to the known methods of analysis, the one being described in this invention distinguishes from the others due to the possibility of keeping the analysed cork stoppers intact and also the possibility of using it by taking into account the industry requirements, since the said method allows 1,000 to 10,000 cork stoppers to be analysed on an hourly basis.

Object of the Invention

A first object of this invention is to provide a method for detection, categorization and separation according to the concentration levels of the volatile analyte (TCA) which causes the so-called "cork taste" to be noticed, wherein:
a) the cork stoppers are separately or jointly taken to the incubation chamber (1) wherein an incubation period begins, and which remains closed during the incubation period by means of a selector valve (2) which will be opened to remove the gas sample for analysis;
b) air or nitrogen is then injected into the incubation chamber (1), dragging the gas enriched in the cork volatile compounds and leading it to the concentration system which contains a trap (4), the latter being at room temperature or at a lower temperature, and concentrates the volatile compounds for analysis by adsorption;

c) the trap (4) is heated to a temperature within the range of 80° C. to 300° C. for a period of time of 10 to 60 seconds, depending on the trap's material characteristics, for desorption of the volatile compounds;

d) the volatile compounds are led by the dragging gas to the detection equipment (6) by means of a heated tube;

e) the detection system (6) registers a signal related to the presence of the analyte, the said signal being used for purposes of classifying the cork stopper or groups of cork stoppers;

f) a software receives the signal and compares it with the established minimum limit, taking the decision of approval of rejection.

Preferably, the incubation is carried out at a temperature within the range of 30° C. to 100° C. and for a variable period of time ranging from 10 seconds to 2 hours, depending on the amount of analyte released by the cork stoppers.

In a preferred embodiment of this invention, the trap (4) is comprised of an adsorbent material and a heating/cooling system which allows the cold/hot cycles to be performed in few seconds, typically from 10 to 60 seconds.

Usually, the trap (4) is heated at a temperature within the range of 120° C. to 300° C. for a period of time of 10 to 20 seconds, for desorption of the volatile compounds.

The method for detection herein disclosed allows 1,000 to 10,000 cork stoppers to be analysed per hour, as well as the detection of the analyte (TCA) in concentrations within the range of ng/L (parts per trillion).

In a preferred embodiment of the invention, the cycle is repeated for each one of the cork stoppers (individually considered or in groups), with the whole cycle being optimized according to the limiting step of obtaining the signal which indicates the presence or absence of the analyte.

Preferably, the optimization of the cycle is performed by means of selector valves which are adequately installed (2), (3), (5) in the circuit, successively leading the flows to the detection system.

A second object of this invention is to provide an installation intended for executing the method of detection, categorization and separation of the volatile analyte (TCA) which is comprised of a:

a) chamber for incubation (1) and conditioning of the cork stoppers to be tested;

b) selector valve (2) of the gas flow from the incubation chamber (1) to the trap (4);

c) selector valve (3) for sending the gas stream to the detector line or for cleaning the circuit.

d) trap (4) with a heating/cooling system;

e) selector valve (5) of the gas flow from the trap (4), of multiple units, to the detection system (6);

f) Detection system (6).

In a preferred embodiment of the invention, the incubation chamber (1) is configured in series and is provided with independent gas flow and heating in each compartment.

Preferably, the trap (4) has high temperature variations, from 80° C. to 300° C., and is provided with material which adsorbs the volatile compounds from the gas stream to be analysed.

EXAMPLES

This invention is hereinafter illustrated with the following examples which have a non-limiting character as regards the protection scope of this patent application.

Example 1

In a carousel-type incubation chamber (1), with 18 positions and a capacity for 30 analysis/hour, the samples, i.e. the cork stoppers, are inserted for a 16-minutes incubation period to be started. The incubation chamber (1) is kept closed during the said period by means of a selector valve (2) which will be opened to remove (suction) the gas sample for analysis, this air being led to the concentration system which contains the traps (4) wherein the volatile compounds concentrate for analysis by adsorption. The samples remain in the traps (4) for 20 minutes. The volatile compounds will be carried to the detection equipment (6) which registers a signal related to the presence of the analyte. The analysis will be performed for 2 minutes/sample.

In this installation 2 traps (4) were used, which allowed a rate of 30 samples/hour.

Example 2

In a carousel-type incubation chamber (1), with 60 positions and a capacity for 180 analysis/hour, the samples, i.e. the cork stoppers, are inserted for a 15-minutes incubation period to be started. The incubation chamber (1) is kept closed during the said period by means of a selector valve (2) which will be opened to remove (suction) the gas sample for analysis, this air being led to the concentration system which is comprised of the traps (4) wherein the volatile compounds concentrate for analysis by adsorption. The volatile compounds will be carried to the detection equipment (6) which registers a signal related to the presence of the analyte. The analysis will be performed for 20 seconds/sample.

In this installation, 6 traps (4) were used which allowed a rate of 180 samples/hour.

As will be evident to a person skilled in the art, several detail modifications can be made, which however shall be included in the scope of this invention.

This invention is to be limited only by the spirit of the following claims.

The invention claimed is:

1. An automated method for detecting a presence and a concentration of a volatile analyte in whole cork stoppers for categorization and separation of the whole cork stoppers according to the analyte concentration, wherein the method comprises at least one cycle in which:
   a) the whole cork stoppers are individually or jointly in a group of whole cork stoppers taken to an incubation chamber, wherein an incubation period begins and wherein the incubation chamber remains closed during the incubation period by means of a selector valve which will be opened to remove a gas sample for analysis;
   b) air or nitrogen is injected into the incubation chamber and the selector valve is opened in order to drag said gas sample and lead it to a concentration system which contains a trap, the latter being at a temperature equal to or lower than room temperature, wherein said concentration system concentrates volatile compounds including the volatile analyte for analysis by adsorption or affinity;

c) the trap is heated to a temperature within a range of 80° C. to 300° C. for a period of time of 10 to 60 seconds, for desorption of the volatile compounds;

d) the volatile compounds are led by a gas configured for dragging said volatile compounds to a detection system by means of a heated tube;

e) said detection system registers a signal related to the presence and concentration of the volatile analyte, the signal being used for purposes of classifying each whole cork stopper or group of whole cork stoppers; and f) a software receives the signal, compares it with a pre-established minimum limit, and makes a decision of approval or rejection of said whole cork stopper or group of whole cork stoppers based on said comparison with the pre-established minimum limit.

2. The method according to claim 1, wherein the volatile analyte is 2,4,6-trichloroanisole (TCA).

3. The method according to claim 1, wherein the incubation period is performed at temperatures within a range of 30° C. to 100° C. and for a period varying from 10 seconds to 2 hours.

4. The method according to claim 1, wherein the trap is provided with an adsorbent material and a heating/cooling system which performs cold/hot cycles in a time period of 10 to 60 seconds.

5. The method according to claim 1, wherein the trap contains no adsorbent material, and a selection of the volatile analyte from a mixture of the volatile compounds with the gas configured for dragging is reached by thermal effect.

6. The method according to claim 1, wherein an optimization of the cycle is performed by means of valves which are duly installed between any element of step a) to d), thereby leading flows of gas samples to the detection system.

7. An installation for executing the method of claim 1, comprising:
   a) an incubation chamber configured for incubation and conditioning of whole cork stoppers to be tested;
   b) a first selector valve configured for providing gas flow from the incubation chamber to the trap, said trap comprising a heating/cooling system which thereby provides temperature variations;
   c) a second selector valve configured for sending a gas stream to the detection system or for cleaning any element of step a) to d); and
   d) a third selector valve configured for gas flow from the trap to said detection system, wherein said detection system provides detection of the volatile analyte.

8. An installation according to claim 7, wherein the trap contains adsorbent material that traps volatile compounds from the gas sample.

* * * * *